(12) United States Patent
Petit et al.

(10) Patent No.: US 7,518,739 B2
(45) Date of Patent: Apr. 14, 2009

(54) USE OF OPTICAL FOURIER TRANSFORM FOR DIMENSIONAL CONTROL IN MICROELECTRONICS

(75) Inventors: Jerome Petit, La Tronche (FR); Patrick Chaton, Theys (FR); Gilles Grand, Grenoble (FR); Thierry Leroux, Caen (FR)

(73) Assignee: Commissariat a l'Energie Atomique, Paris (FR)

( * ) Notice: Subject to any disclaimer, the term of this patent is extended or adjusted under 35 U.S.C. 154(b) by 73 days.

(21) Appl. No.: 10/571,697

(22) PCT Filed: Sep. 17, 2004

(86) PCT No.: PCT/FR2004/050443

§ 371 (c)(1),
(2), (4) Date: Mar. 13, 2006

(87) PCT Pub. No.: WO2005/026707

PCT Pub. Date: Mar. 24, 2005

(65) Prior Publication Data

US 2007/0064247 A1   Mar. 22, 2007

(30) Foreign Application Priority Data

Sep. 17, 2003   (FR) .................................. 03 50560

(51) Int. Cl.
*G01B 11/14* (2006.01)
(52) U.S. Cl. .................................................. 356/625
(58) Field of Classification Search .............. 356/613, 356/625, 328
See application file for complete search history.

(56) References Cited

U.S. PATENT DOCUMENTS

| 4,678,332 | A | * | 7/1987 | Rock et al. ............... 356/328 |
| 4,735,487 | A | | 4/1988 | Thorwirth et al. |
| 4,999,014 | A | | 3/1991 | Gold et al. |
| 5,241,369 | A | | 8/1993 | McNeil et al. |
| 5,428,442 | A | | 6/1995 | Lin et al. |
| 5,880,845 | A | | 3/1999 | Leroux |
| 6,020,957 | A | | 2/2000 | Rosengaus et al. |
| 2005/0200859 | A1 | | 9/2005 | Hazart |

FOREIGN PATENT DOCUMENTS

FR    2 613 830    10/1988

(Continued)

OTHER PUBLICATIONS

Moharam, M.G. et al., "Formulation for stable and efficient implementation of the rigorous coupled-wave analysis of binary gratings", J. Opt. Soc. Am., vol. 12, No. 5, pp. 1068-1076, 1995.

(Continued)

*Primary Examiner*—Roy M Punnoose
*Assistant Examiner*—Isiaka O Akanbi
(74) *Attorney, Agent, or Firm*—Oblon, Spivak, McClelland, Maier & Neustadt, P.C.

(57) ABSTRACT

A device for measuring the dimensional or structural characteristics of an object. A detector forms an optical Fourier transform image of an elemental surface of the object in an image focal plane. A processor produces data relating to at least one dimensional and/or structural characteristic of the object from the information provided by the detector.

48 Claims, 11 Drawing Sheets

FOREIGN PATENT DOCUMENTS

| | | |
|---|---|---|
| FR | 2 749 388 | 12/1997 |
| FR | 2 777 653 | 10/1999 |
| FR | 2 833 743 | 6/2003 |
| FR | 2 849 181 | 6/2004 |
| FR | 2 849 504 | 7/2004 |
| FR | 1 598 647 | 11/2005 |

OTHER PUBLICATIONS

Allgair, John et al., "Implementation of Spectroscopic Critical Dimension (SCD™) for Gate CD Control and Stepper Characterization", Proceedings of SPIE, Vo. 4344, pp. 462-471, 2001.

Baum, Chris C. et al., "Scatterometry for Post-etch Polysilicon Gate Metrology", SPIE, vol. 3677, pp. 148-158, 1999.

Neviere M. et al., "Grating Electromagnetic Theory User Guide", Journal of Imaging Science and Technology, vol. 41, No. 4, pp. 315-323, 1997.

B.E.A. Saleh et al., "Fundamental of Photonics, Wiley series in pure and applied optics", John Wiley and Sons, pp. 124-127, 1991.

Moreau, Olivier et al., "Fast and accurate measurement of liquid crystal tilt bias angle with ELDIM EZContrast system", Proceedings of the SPIE, Int. Society for Optical Engineering, pp. 236-241, 1999.

* cited by examiner

USE OF OPTICAL FOURIER TRANSFORM FOR DIMENSIONAL CONTROL IN MICROELECTRONICS

TECHNICAL FIELD AND PRIOR ART

This invention relates to the field of dimensional inspection and applies in particular to the geometric characterisation of small structures (of the order of a µm or less, for example between 1 µm and 10 nm) by analysis of diffracted light, or scatterometry.

Among possible applications of the present invention may be mentioned the characterisation of heterogeneous nanostructures implemented generally in microelectronics technology such as test patterns (etched gratings) and/or the characterisation of multi-layer deposit structures. These nanostructures may be one-dimensional or two-dimensional gratings (contact or pin gratings for example), or single layers or layer stacks or single or bi-periodic layer stacks and gratings.

It also relates to structures such as biomimetic structures, or structures of the "overlay" type (superimposed gratings with offset).

Known dimensional inspection methods are methods of scatterometry by ellipsometry and by photogoniometry.

These optical methods are reproducible, quite fast and non-destructive.

In the case of a grating measurement, they use the grating diffraction effect and thus give mean characteristics of the grating lines as indicated in Chris C. Baum et al. "*Scatterometry for Post-etch Polysilicon Gate Metrology in SPIE Metrology, inspection and Process control for monolithography*". 1999, and in J. Allgair et al. "*Implementation of Spectroscopic Critical Dimension for gate CD Control and Stepper Characterisation*", in *SPIE Metrology, inspection and Process control for monolithography*, 2001.

Spectroscopic ellipsometry is a surface characterisation technique that takes advantage of the change of polarisation state of the light upon reflection on the surface. This change of state for different wavelengths and a fixed angle of incidence make it possible to return to the optical characteristics of the sample. A description of this is given for example in J. Allgair et al. "*Implementation of Spectroscopic Critical Dimension for gate CD Control and Stepper Characterisation*", in *SPIE Metrology, inspection and Process control for monolithography*, 2001.

Photogoniometry is a surface characterisation technique. It is described in the article by Chris C. Baum et al. cited above, and uses the variation in the reflectivity of the specular order of a grating as a function of the angle of incidence of the beam. Use is also made of the fact that the behaviour of the light differs according to the polarisations in order to double the quantity of usable data.

These known methods of optical methodology use a monochromatic or polychromatic light beam.

In the first case the angle of incidence is the variable parameter of the final measurement. In the second case the angle of incidence is fixed and the wavelength is variable in the final measurement.

The first case is implemented using a goniometer the position of which is changed between each measurement point, or, more rapidly, using a photodiode array.

The second case employs a monochromator which scans each measurement point in succession, or a spectrograph.

The grating signature is then obtained. The characteristics of the lines of the grating can then be found, either by finding the nearest theoretical signature in a library of pre-calculated signatures, or by calculating the nearest theoretical curve, as described for example in M. G. Moharam et al. "*Formulation for stable and efficient implementation of the rigourous coupled-wave analysis of binary gratings*", Journal of Optical Society of America, 1995. 12(5): pp 1068-1076, in M. Neviere et al. "*Grating Electromagnetic Theory User Guide*", Journal of imaging science and technology, 1997. 41(4): pp 315-323 and in the article by J. Allgair et al. already cited above.

These methods are relatively fast, with the time between the moment when the object is captured and the result being a few seconds (5 to 11 s), which is compatible with a production environment; but the quantity of data provided is generally not sufficient to provide an exact characterisation of the objects being investigated.

The problem therefore arises of finding a new process and a new device that allow a determination of the dimensional and/or structural characteristics of objects, for example of the type implemented in microelectronics, preferably within a time compatible with an environment for the production of such objects and that provide sufficient data.

Furthermore, another problem is that conventional ellipsometry and goniometry devices use cumbersome measurement arms and employ mobile mechanical parts.

In fact, in a field such as microelectronics or in the field of nanostructures, particularly in a production environment, the space requirement and/or the simplicity of a control system are important parameters.

DISCLOSURE OF THE INVENTION

The invention aims to resolve this problem.

The subject of the invention is an optical system, a device and a process that allow a determination of the structural characteristics of an object.

The invention relates to a device for measuring the dimensional and/or structural characteristics of an object, comprising:

means for forming an optical Fourier transform image of an elemental surface of the object on an element or detection means or on a plane equipped with detection means, processing means for producing data in relation to at least one dimensional and/or structural characteristic of the object, or for identifying such a characteristic, from information provided by the detection means.

The invention therefore employs an optical Fourier transform of the light, or of radiation, diffused or diffracted by the object or sample being examined.

The means for forming an optical Fourier transform image of an elemental surface of the object are preferably means for forming an image of this optical Fourier transform in a Fourier image focal plane.

The device may additionally comprise means for defining the geometry of said elemental surface.

Preferably, these means allow this elemental surface to be defined independently of the numerical aperture of the means so as to form an optical Fourier transform image of a surface of the object.

The device may also comprise transfer means for forming the optical Fourier transform image of the elemental surface on detection means.

According to the invention the optical Fourier transform (OFT) technique is used therefore for an application for the characterisation of structures, in particular nanostructures, of characteristic sizes of between for example 1 µm and 10 nm.

OFT allows a response to be obtained from the illuminated object in a single acquisition. Measurement is therefore very fast and a single measurement gives a very great quantity of information whereas the other methods give only a limited amount of information.

Furthermore the system according to the invention takes up very little space and employs almost no mobile mechanical parts, which simplifies its use.

A radiation source for illuminating the object will preferably be a source that is spatially non-coherent, monochromatic or of small spectral width, preferably less than 10 nm.

The power of this source will be a function of the measurement time and of the selected geometry of the elemental surface. Preferably it is between 100 mW and 500 mW.

The system may comprise a device for controlling polarisation before and after reflection on the surface of the sample.

The processing means employ for example an RCWA calculation.

They may also calculate a theoretical reflected intensity distribution, for a given incident light and given dimensional and/or structural characteristics of the object, then compare this theoretical distribution with a reflected intensity distribution and modify the given dimensional and/or structural characteristics of the object if the result of the comparison is not satisfactory.

The invention also relates to a process for measuring dimensional or structural characteristics of an object whose surface is illuminated by radiation, which implements a device as described above.

The invention also relates to a process for measuring dimensional or structural characteristics of an object whose surface is illuminated by radiation, which comprises:
- forming an optical Fourier transform image of an elementary surface of the object on detection means, for example in a Fourier image focal plane then on or in a plane equipped with detection means,
- processing data provided by the detection means so as to produce at least one datum relating to at least one dimensional and/or structural characteristic of the object.

BRIEF DESCRIPTION OF THE FIGURES

FIGS. 6A to 13C are comparative examples.

DETAILED DISCLOSURE OF EMBODIMENTS OF THE INTERVENTION

Figure 1A:
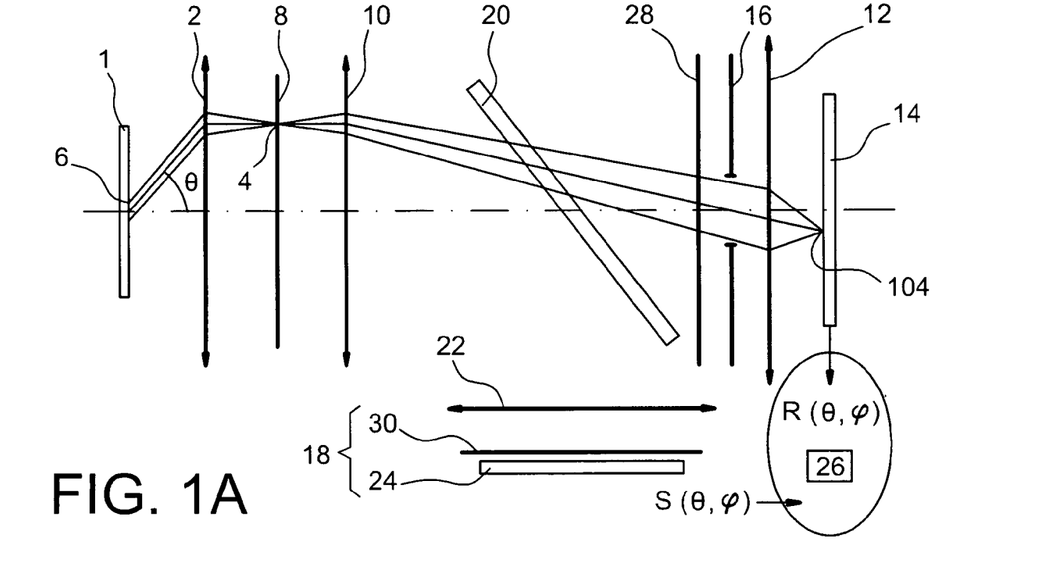
FIGS. 1A and 1B show an embodiment of the invention.

One embodiment of the invention is shown in FIG. 1A.

A measurement objective 2 allows the Fourier transform image 4 of an elemental surface 6 of an object 1 to be formed in its image focal plane 8.

This surface is illuminated using a radiation source 24, and it may be defined by means, for example a diaphragm, in order to restrict the measurement zone.

Optical Fourier transform (OFT) is an optical method that allows an image to be made of the angular response of a sample to light excitation.

According to the invention the angular Fourier transform of the light reflected or diffracted by a sample can be viewed.

The object 1 is for example a one-dimensional or two-dimensional grating (for example a contact or a pin grating) or a layer stack or a combination of a layer stack and of one or more single or bi-periodic gratings. It may also be a single layer whose thickness or index need to be identified.

The characteristic magnitudes of these structures are preferably:
for gratings, between 1 µm or 500 nm or 100 nm and 50 nm or between 50 nm and 10 nm,
and, for layers, between 100 µm and 10 nm or even 1 nm.

Figure 1B:
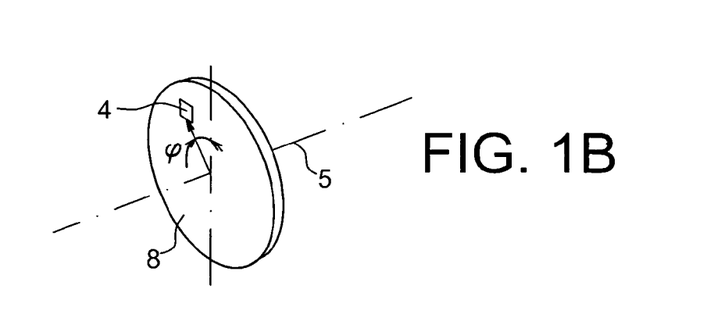

A transfer objective then forms the Fourier transform image of the elemental surface 6 on a sensor 14 made up of detectors. This sensor 14 is for example a CCD camera. It allows the intensity emitted by an elemental zone 6 to be picked up, along each direction of emission identified by the pair ($\theta$, $\phi$) as shown in FIGS. 1A and 1B.

In the image focal plane 8 (FIG. 1B) the distance between the optical axis 5 and the zone 4 where the plane waves emitted from the zone 6 according to the angle $\theta$ are focused, is in proportion to $\theta$. The azimuth $\phi$ corresponds to the azimuthal direction of emission from this zone 6.

The use of a CCD camera makes it possible to acquire, in a single acquisition, as much data as there are pixels illuminated by the CCD camera.

The transfer objective comprises for example a pair of lenses 10, 12. The lens 10 may be a field lens which gives a real image in the vicinity of the plane of a diaphragm 16 or in this plane.

This diaphragm allows the aperture of the elemental surface 6 to be defined. It has for example a diameter of more than 20 µm or between 20 µm or 40 µm and 500 µm, for example equal to about 300 µm. This diaphragm is located in or in the vicinity of a conjugate plane of the plane of the object 1.

This diaphragm can be replaced by any optical means, for example a re-dimensioning of the optics, which allows the illuminated zone of the sample to be restricted.

This diaphragm or this optical means allows the size of the analysed surface 6 to be adjusted, independently of the angular aperture (maximum angle of the rays that can be collected by the device), or of the numerical aperture of the device (cosine of this angle).

It is thus possible to define sizes of elemental surface that are sufficiently large to include very numerous elemental patterns of the grating (size of the zone or of the surface 6 greater than 20 µm, whereas the elemental patterns can be as small as a few nm, for example between 10 nm and 50 nm), for example one or several hundreds of elemental patterns, and therefore to ensure that the diffraction effect is efficient even if the angular aperture of the device is very large (up to ±80° or ±88°).

The device therefore employs an optical system that comprises a first objective lens 2, a diaphragm (or optical means allowing the illuminated zone of the sample or elemental surface 6 to be restricted), and a second (transfer) objective lens.

It is possible, by using this device, to adjust independently the size of the spot on the surface 1 (using the diaphragm or equivalent means) and the numerical aperture of the first objective lens 2.

Measurements can therefore be taken at a significant angle (up to 88°) on a lit up surface of reasonable size, for example with a diameter of about 25 µm or one included in one of the ranges already mentioned above).

According to one embodiment, a device according to the invention employs:

- a first objective lens, or means forming a first convergent objective lens, to form the Fourier transform image of an elemental zone of an object, in the image focal plane of the first objective lens,
- a second convergent objective lens or second means forming a second convergent objective lens, to project or transfer this image towards or onto a two-dimensional detector,
- means, which may be situated in proximity to the second objective lens, to stop down or diaphragm or define an elementary surface; preferably these means can be adjusted independently of the numerical or angular aperture of the first objective or means forming a first objective.

Illumination can be achieved from a Fourier plane 18, offset from the axis of the device by a semi-transparent plane 20. Each point on the surface of this Fourier plane thus corresponds to an angle of incidence or an azimuth on the tested sample.

The lens 22 fulfils the same function as the lens 12 in the case of the direct path.

The radiation source 24 is preferably, from the spatial point of view, non-coherent or only slightly coherent, in order to eliminate the "speckle" effect. This is an interference phenomenon from the source points or pixels, which randomly scrambles measurements. There is a clear difference in signal quality between measurements taken with "speckle" and without "speckle".

This source is preferably an extensive source placed in a conjugate plane of the Fourier plane to form an illumination Fourier plane.

The source is preferably high-powered (power for example of between 100 mW and 500 mW), so as to allow the sample to be illuminated via the diaphragm. But this power will depend on the geometry selected for each elemental surface to be illuminated, so as to perform a measurement within a selected measurement time, for example of less than 1 second.

Finally, it is preferably monochromatic or of small spectral width, less than 10 nm.

This source may be a laser (for example a doubled NdYag laser at 532 nm) operating continuously, decohered (for example using a revolving depolished plate), or a series of superluminescent diodes or laser diodes.

Calculation means 26 allow the data received on the sensor 14 to be processed and employ a data-processing process. These means comprise for example a micro-computer specially programmed to implement such a process. This process allows the dimensional and/or structural characteristics of the examined object 1 to be found and will be explained in detail hereinafter.

Preferably, the device comprises a polariser 28 allowing the polarisation of the diffracted light to be selected.

Additionally, the use of a mask 30 in the Fourier illumination plane allows the illumination angles (θ, φ) to be selected.

Figure 2A:
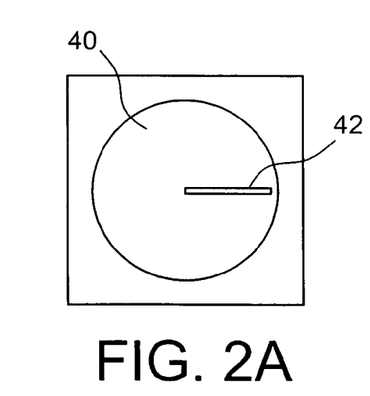
FIGS. 2A and 2B are examples of masks that can be used in the context of the present invention.

According to one example, illustrated in FIG. 2A, a mask 40 has a slot 42 allowing a so-called "theta" measurement to be taken, for example with an angle θ of between a few degrees and a few tens of degrees, for example between 8° and 80° or 88°.

Figure 2B:
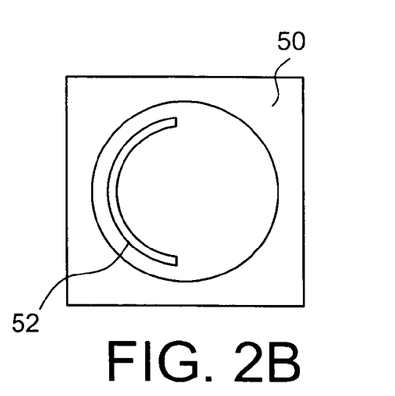

According to another example illustrated in FIG. 2B, a mask 50 has a slot 52 in a circle arc, making it possible, for a given angle θ, to take a purely azimuthal, so-called "phi" measurement, for example with an angle φ of between 0° and 180°, for an angle θ here equal to about 70°.

Other forms of masks are possible.

The use of masks allows a selective illumination of the surface of the object, by selecting the angles θ and/or φ.

The invention therefore in particular allows measurement under illumination with a fixed or a variable azimuth φ, or an azimuth comprised between two limit values, the angle θ itself being fixed or variable or comprised between two limit values (for example between 0 and 80° or 88°).

One advantage of being able to select zones with a high angle θ (up to 80° or 88° for example) is that these zones are zones of high sensitivity.

A polariser may also be provided at the input of the device.

Means for illuminating a sample may therefore comprise:

- a beam separation device such as a mirror or a separator cube,
- an objective lens (the third if the device already comprises two objective lenses as indicated above), to re-image the FT image on a second plane, the so-called illumination Fourier plane,
- possibly a mask, to select angles of illumination on the sample,
- a light source in the illumination Fourier plane, which preferably lights up the whole Fourier plane.

A very flexible control of the sample can be obtained with these means.

The response of the detector 14 is then processed so as to extract the data that allows the object 1 to be characterised in terms of dimension and/or structure.

It may for example be a matter of a dimension in a direction non-parallel to the plane of the object 1, or perpendicular to this plane, for example the thickness of a layer of silicon.

It may also be a matter of determining the structural characteristics of a two-dimensional grating, for example a biomimetic structure.

The characterisation will therefore allow characteristics of contours and/or dimensions of certain structures to be determined.

The invention employs a so-called RCWA (Rigorous Coupled Wave Analysis) analysis technique. A technique of this type is described in references 3 and 4.

This method allows four parameters or pieces of data to be obtained: $R_{SS}$ (reflection coefficient of a polarisation S the direction S being defined by the polariser 28), $R_{PP}$ (reflection coefficient of a polarisation P perpendicular to S), $R_{SP}$ (coefficient of coupling, after reflection, of a polarisation S to the polarisation P), $R_{PS}$ (coefficient of coupling, after reflection, of a polarisation P to the polarisation S).

Use is made, in the context of the present invention, not of these four pieces of data, but of the data $P_0$ and $P_{90}$, which are standardised polarisation intensities obtained from $R_{PP}$, $R_{SS}$, $R_{SP}$ and $R_{PS}$ according to the formulae:

$$P0 = |\cos(\phi) \cdot R_{pp} + \sin(\phi) \cdot R_{sp}|^2 + |\cos(\phi) \cdot R_{ps} + \sin(\phi) \cdot R_{ss}|^2$$

$$P90 = |\cos(\phi) \cdot R_{sp} - \sin(\phi) \cdot R_{pp}|^2 + |\cos(\phi) \cdot R_{ss} - \sin(\phi) \cdot R_{ps}|^2$$

Figure 3:
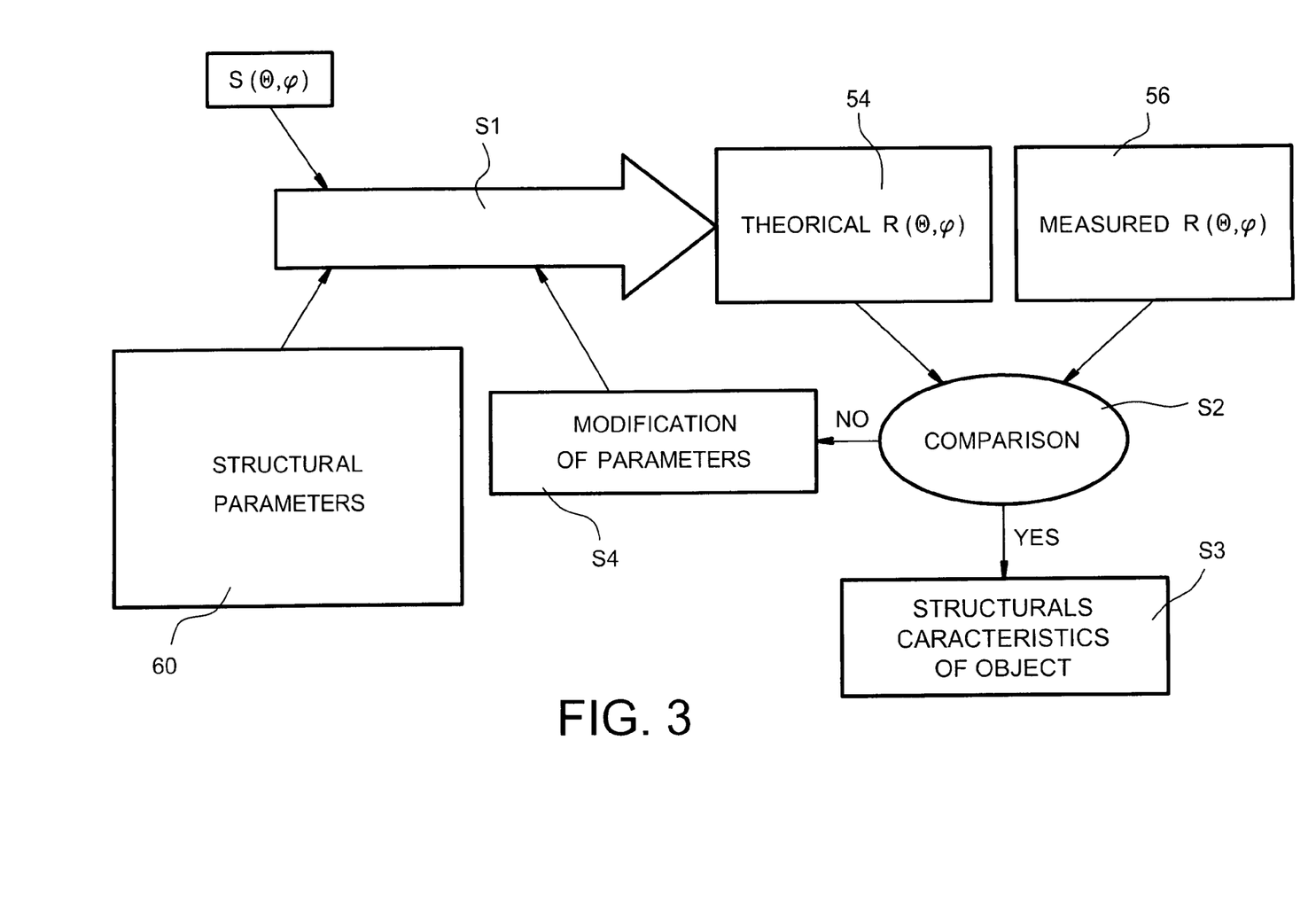
FIG. 3 is a block diagram of a characterisation process.

FIG. 3 shows the steps in a data-processing process according to the invention.

Data S (θ φ) on the incident light is subjected, with approximate structure parameters 60 (for example height and/or width of the lines of a grating and/or slope of walls or profiles of these lines, and/or thickness of the layer or layers, index of the material or materials) to processing by the RCWA method (step S1). This theoretical calculation provides a theoretical signature R (θ φ), which represents the reflected light theoretically measured on the sensor. R (θ φ) is composed, in the case of a grating, of the specular reflection $R_0$ and the diffracted orders $R_n$:

$$R(\theta, \varphi) = R_0(\theta, \varphi) + \sum_n R_n(\theta, \varphi).$$

The theoretical signature, or intensity distribution, resulting from the calculation is compared (step S2) with the measured signature 56 of the reflected light. The comparison is for example made using a regression method, comparing the theoretical signature and the measured signature, for example at φ, of the intensities $P_0$ and $P_{90}$ (obtained by positioning an analyser placed in front of the detection means 14).

If the agreement obtained according to this criterion is good, the characteristics 60 introduced into the RCWA calculation (S3) may be considered as the characteristics of the measured object 1.

If the agreement obtained according to this criterion is not good, the parameters 60 are modified (step S4), and a new RCWA calculation is made until satisfactory agreement is obtained.

In other words, $P_0$ and $P_{90}$ profiles may be established as a function of the azimuth φ and/or of the angle θ and compared with $P_0$ and $P_{90}$ profiles for a theoretical structure. One or more characteristics of the theoretical structure (for example: grating pitch or layer thickness) may be gradually modified (step S4) so that the theoretical profile gets near to the measured profile. When satisfactory agreement is obtained, the structural characteristics of the object can be identified.

In certain cases it will also be possible to use the profiles of the coefficients $R_{PP}$ and $R_{SS}$ as a function of θ, the processing of the data being the same as that disclosed above. This is particularly the case when characterising the thickness of a single layer.

The invention brings a certain number of advantages.

Firstly, measurement is fast (300 ms) and allows sufficient information to be provided. Only a single acquisition is required with a CCD camera 14 making the Fourier transform image. Furthermore the use of a CCD camera allows the data to be processed in parallel and not in succession as with a conventional sensor.

A very large quantity of information is therefore obtained and acquisition is no longer a limiting factor during characterisation.

Furthermore the invention allows a very large quantity of information to be collected in a single acquisition, much more than by conventional processes. For example it allows the diffracted orders to be characterised and therefore additional information to be drawn from them (surface roughness, etc.). Lateral roughness may also be deduced from the light diffused outside the specular order and from the diffraction orders over which it appears as a second order effect.

In terms of space requirement, the device can be reduced to a volume of about a few dm³, since it consists merely of a source 24, optical elements and a detector 14. Conventional ellipsometry and goniometry devices use cumbersome measurement arms. In a field such as microelectronics or in the field of nanostructures, this parameter is important. It should be added that there is an almost complete absence of mobile mechanical parts.

The invention allows access to azimuthal goniometric data: the measurement as a function of φ gives relevant information for characterising three-dimensional (particularly as regards contact or pin gratings, or biomimetic membranes) or asymmetrical structures.

The use of goniometric data has an additional advantage, compared with ellipsometric data, in that no knowledge is required of the material dispersion curve.

Furthermore, it is possible, by varying the azimuth φ, to vary the apparent period and therefore to measure gratings with a smaller pitch.

Furthermore, the possibility of collecting all the angles of incidence but also all the azimuths allows all the polarisation orientations to be measured simultaneously, which allows all the diffraction orders to be recovered and greater sensitivity to be obtained.

To that should be added the possibility of taking measurements with different wavelengths. To do this different sources can be used, and particularly a laser (for example at 532 nm or at 633 nm), or a white light source (for example a xenon lamp) fitted with an interferential filter, or a super-luminescent diode matrix, or laser diodes.

Table 1 below recapitulates data relating to a process according to the invention (OFT), to an ellipsometry process (a "multi-spectral" technique, employing several wavelengths and, for each wavelength, the reflection is measured) and to a "conventional" process (with a high-performance ellipsometer, a single wavelength per measurement and several successive measurements).

| Method | OFT | Multi-spectral | Conventional |
| --- | --- | --- | --- |
| Measurement time (one measurement) | 300 ms | 100 ms | a few ms |
| Number of measurements | 1 | 1 | 200 |
| Total acquisition time | 300 ms | 100 ms | From 500 ms to 2 s |
| Sensor | CCD camera 1M pixels | CCD array | Photo-sensitive cell |
| Quantity of data | 1 million | >500 | 200 |

It can clearly be seen that the process according to the invention allows a much greater quantity of data to be obtained than known processes.

The invention may be associated with a production unit for components like those made in microelectronics. The object 1 comes from this production unit, passes in front of a device such as the one described above in connection with the figures, with the data-processing means 26 comprising for example a micro-computer and being specially programmed to apply a processing process as described above. An operator can thus get the analysis result at the production site itself and modify it as a consequence if the analysis indicates dimensional and/or structural characteristics that differ from those expected.

Optical means that can be employed in the context of the invention are also described in FR 2 613 830 and U.S. Pat. No. 5,880,845, which are incorporated by reference.

Examples of measurements taken with a process according to the invention will now be given.

EXAMPLE 1

Example of Overall Measurement

Figure 4:
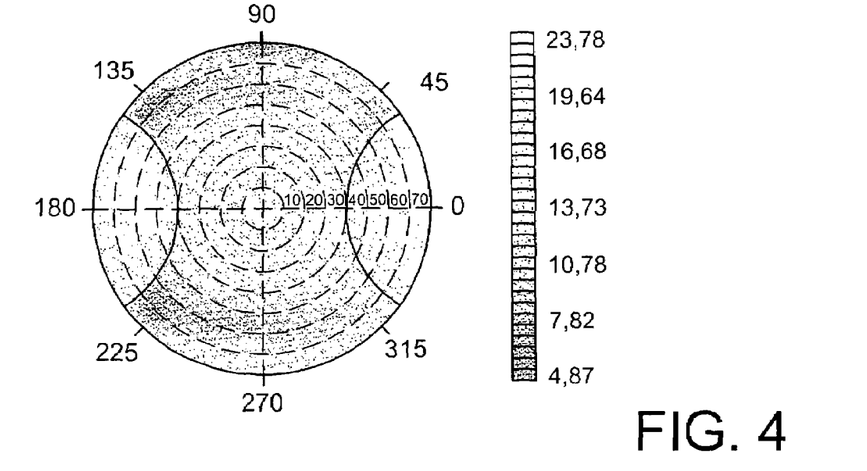
FIG. 4 shows the result of the overall illumination of a grating with a device according to the invention.

FIG. 4 shows the result of the overall illumination of a grating, the disc representing the surface of the azimuthal (φ from 0 to 360°) and radial (θ from 0 to 80°) angles, the level of grey representing the diffracted luminous intensity.

This measurement shows the very large quantity of data obtained in a single acquisition, this quantity only being limited by the number of elementary sensors of the detector 14; a detector comprising approximately 1 million pixels, for example a conventional CCD camera, allows 1 million pieces of data to be obtained (as against 200 conventionally for another method, see table 1 above).

EXAMPLES 2-1-2-8

Examples of Selective Measurements

As mentioned previously, one of the features of the invention is the use of selective masks allowing only data that is strictly necessary to be selected.

Figure 5A:
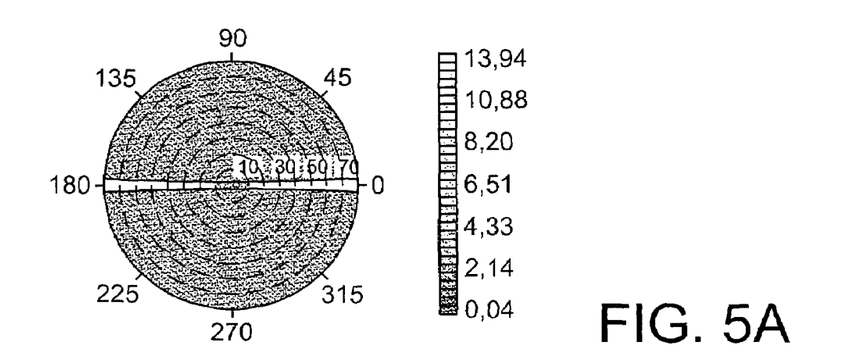
FIGS. 5A and 5B show the result of illuminating a grating with a device according to the invention, equipped with two different masks.
Figure 5B:
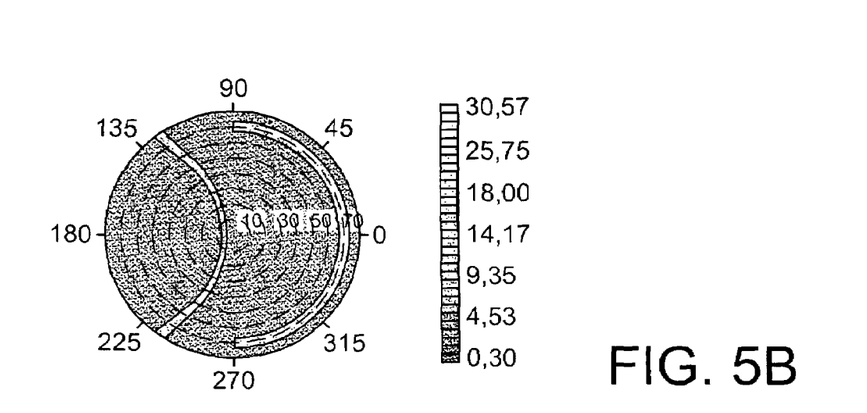

FIGS. 5A and 5B show results of selective measurements taken with the masks in FIGS. 2A and 2B respectively, on etched resin gratings. The wavelength of the source is here 532 nm.

Generally speaking, the appearance of orders other than the specular order brings additional information that cannot be obtained with other scatterometry methods. The characteristics given in the following examples have nonetheless been achieved with the specular order. The following definitions are used:

f: fill factor=width of lines in the grating;
H: height of the lines
GOF: goodness of fit or figure of merit, calculated as a function of $X^2$ (GOF=$1-X^2$), with $X^2$ being the error between the simulation and the measurement ($X^2=(P_{0exp}-P_0)^2 + (P_{90exp}-P_{90})^2$). The coefficient GOF gets closer to 1 the better the regression.

EXAMPLE 2-1

Figure 6A:
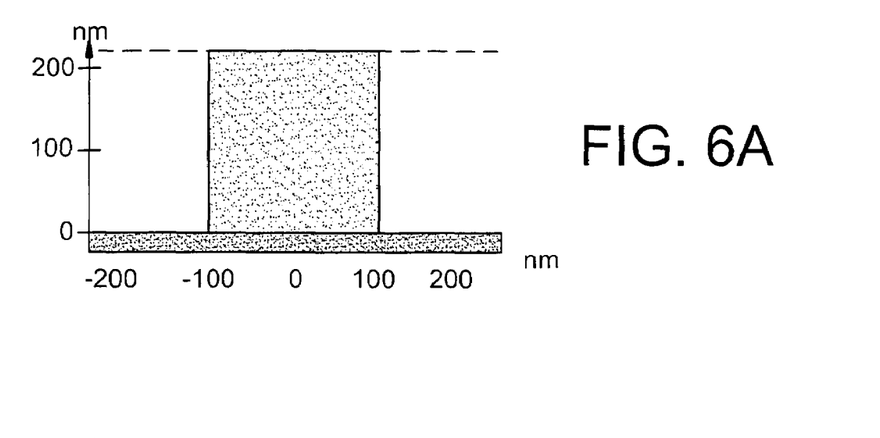
Figure 6B:
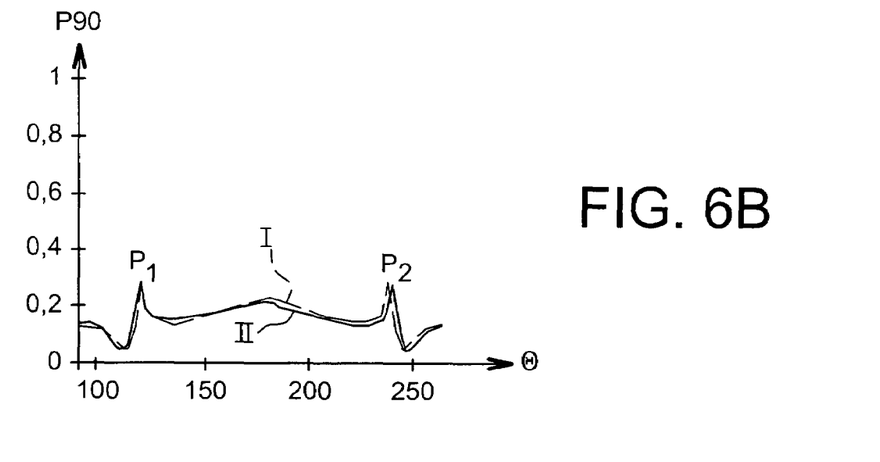
Figure 6C:
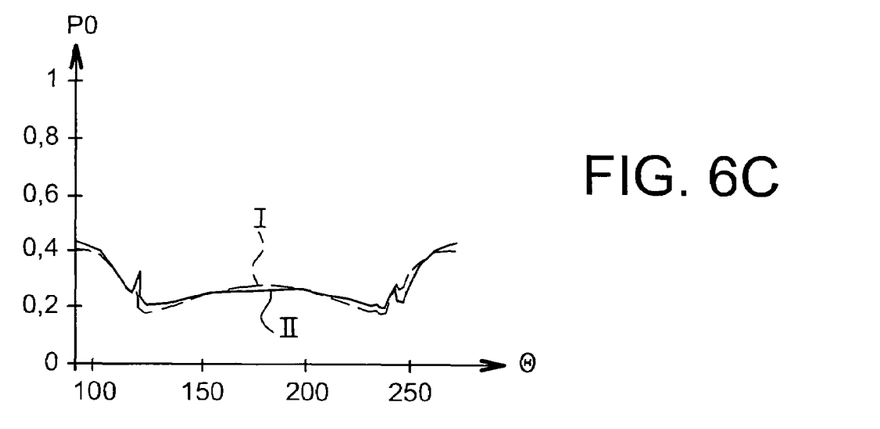

This example is shown in FIGS. 6A to 6C. It relates to the characterisation of a resin grating the profile of which is shown in FIG. 6A. This grating has, theoretically, a line width of 250 nm for a period of 500 nm (250/500 nm). This measurement has been taken for $\theta=70°$ and with two different polarisers. FIGS. 6B and 6C show the variations of $P_{90}$ and $P_0$ respectively as a function of $\phi$, the curve I being the simulated curve, the curve II the measurement curve. In these two figures two grating resonance peaks $P_1$, $P_2$ can clearly be seen. An agreement, it too quite clear, appears between the two curves I and II.

$f(1)=212.2; h(1)=223.9$ $GOF(x2)=0.99983$

EXAMPLE 2-2

Figure 7A:
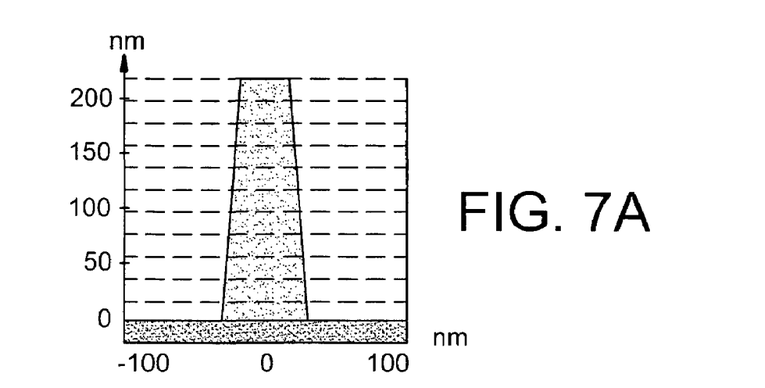
Figure 7B:
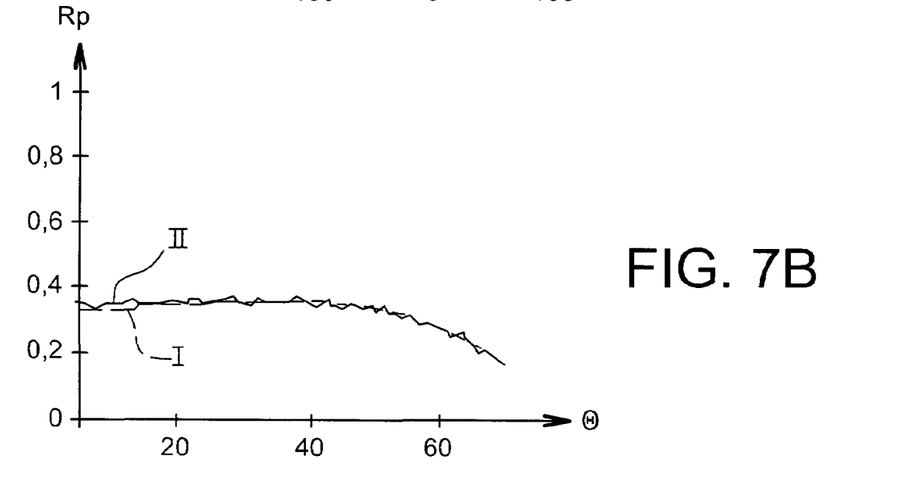
Figure 7C:
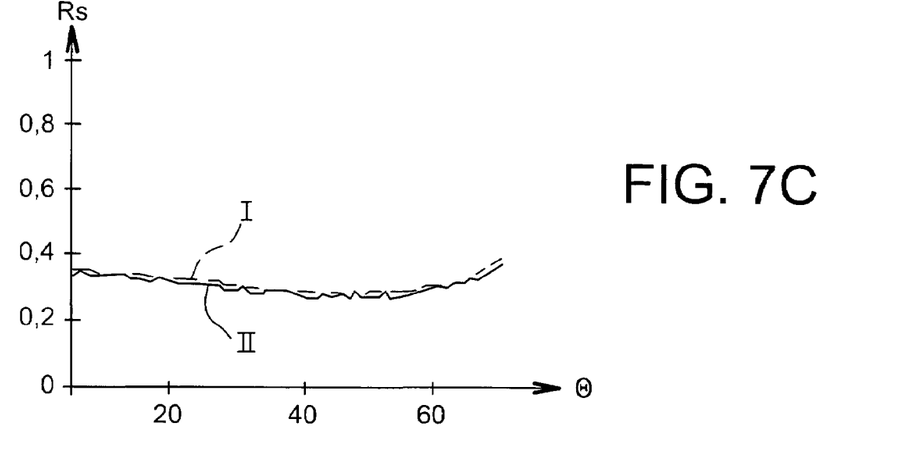

This example is shown in FIGS. 7A to 7C and relates to the characterisation of a resin grating with a width of 70 nm and a period of 240 nm (the profile of which is shown in FIG. 7A). This measurement was taken for $\phi=0°$ and $\theta$ varying from 8 to 68°. In FIGS. 7B and 7C, showing the variations in $R_P$ and $R_S$ respectively as a function of $\phi$, the curve I is the simulated curve, and the curve II the measurement curve. A comparison of these two figures with FIGS. 6B and 6C clearly shows that the sensitivity and accuracy obtained are better with the use of the parameters $P_0$ and $P_{90}$.

$f(1)=53.8; h(1)=212.1; theta (1)=86.5$ $GOF(x^2)=0.99997$

EXAMPLE 2-3

Figure 8A:
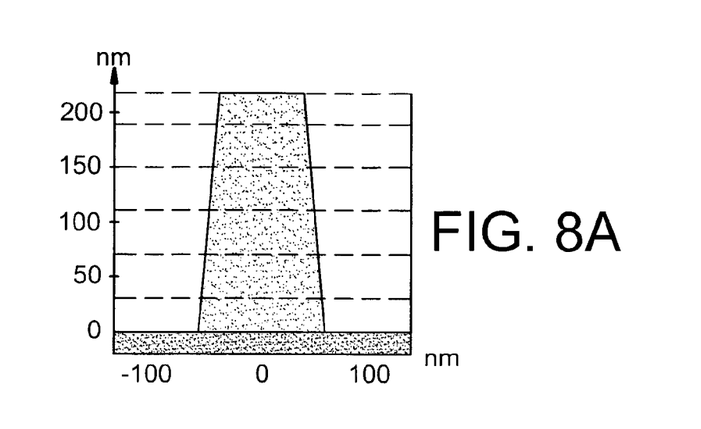
Figure 8B:
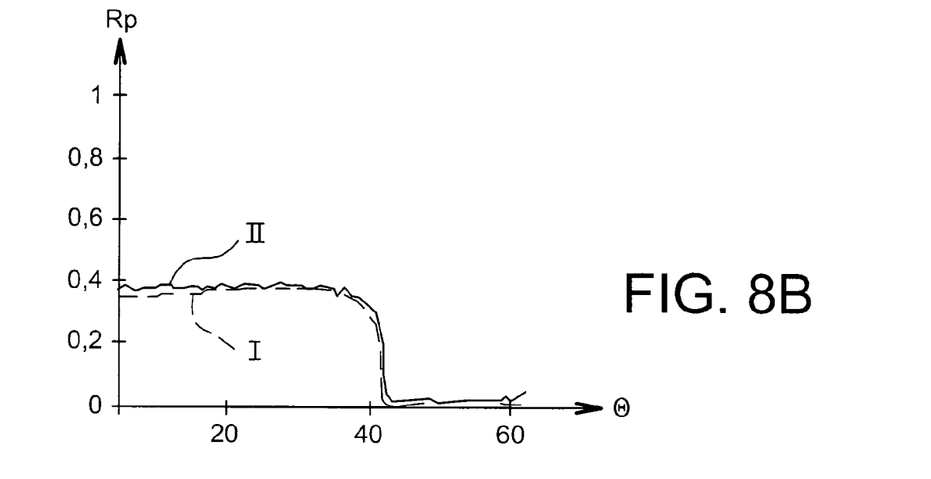
Figure 8C:
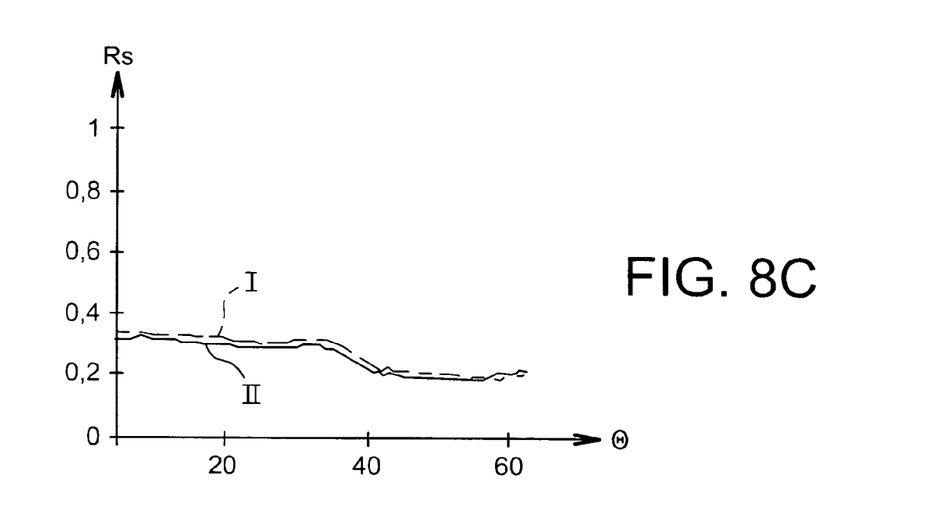

This example is shown in FIGS. 8A to 8C and relates to the characterisation of a resin grating with a width of 130 nm and a period of 320 nm; this measurement was taken for $\phi=0°$ and $\theta$ varying from 8 to 62°.

In FIGS. 8B and 8C, the curves $R_P$ and $R_S$ are given as a function of $\theta$. The measurement curve is the curve II and the theoretical curve the curve I.

This example shows a good agreement between measured curve and theoretical curve. However, in this case too, accuracy is better with $P_0$ and $P_{90}$.

$f(1)=108.7; h(1)=221.9; theta (1)=87.9$ $GOF(x^2)=0.99988$

EXAMPLE 2-4

Figure 9A:
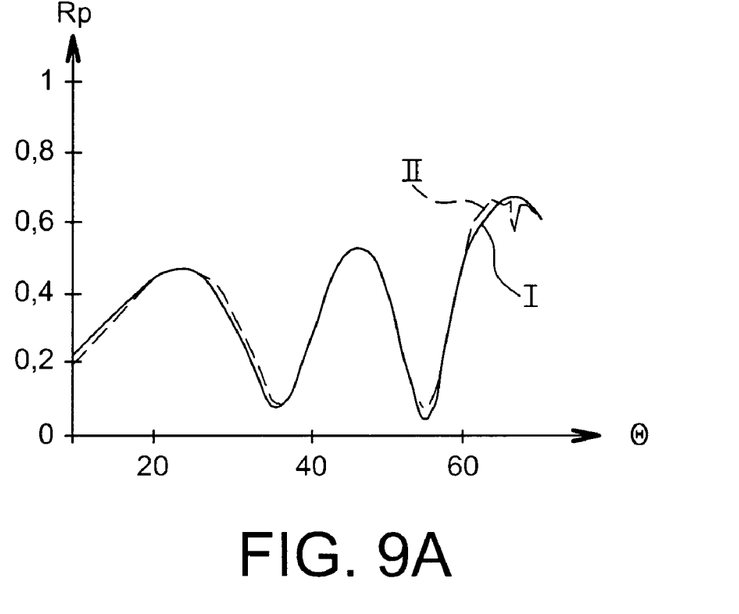
Figure 9B:
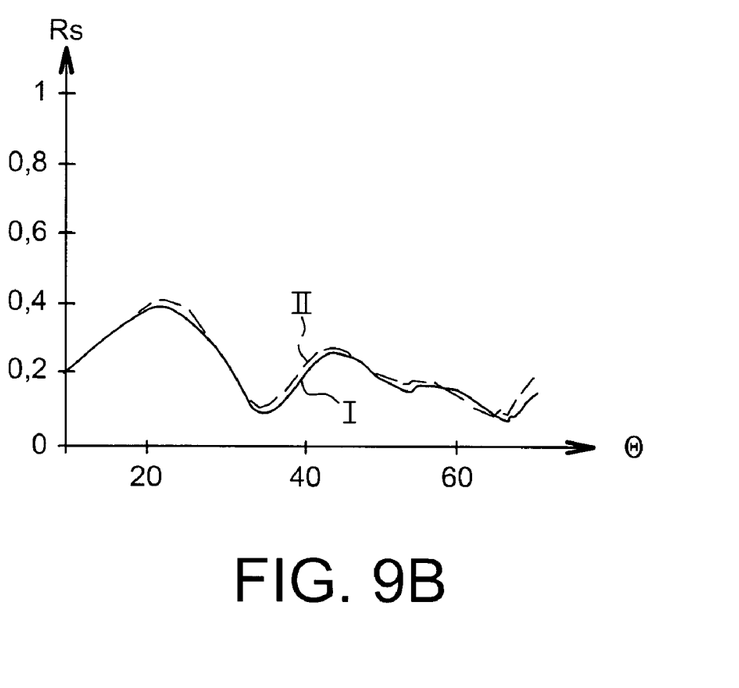

This example is shown in FIGS. 9A and 9B and relates to the characterisation of a double layer of silicon nitride (142 nm) on silica (1870 nm). The substrate is silicon.

In FIGS. 9A and 9B, the curves $R_P$ and $R_S$ are given as a function of $\theta$. The measurement curve is the curve II and the theoretical curve the curve I.

This example shows that the invention allows thicknesses of a multi-layer structure to be identified.

$h(1)=1853.4; h(2)=155.5$ $GOF(x^2)=0.99989$

EXAMPLE 2-5

Figure 10A:
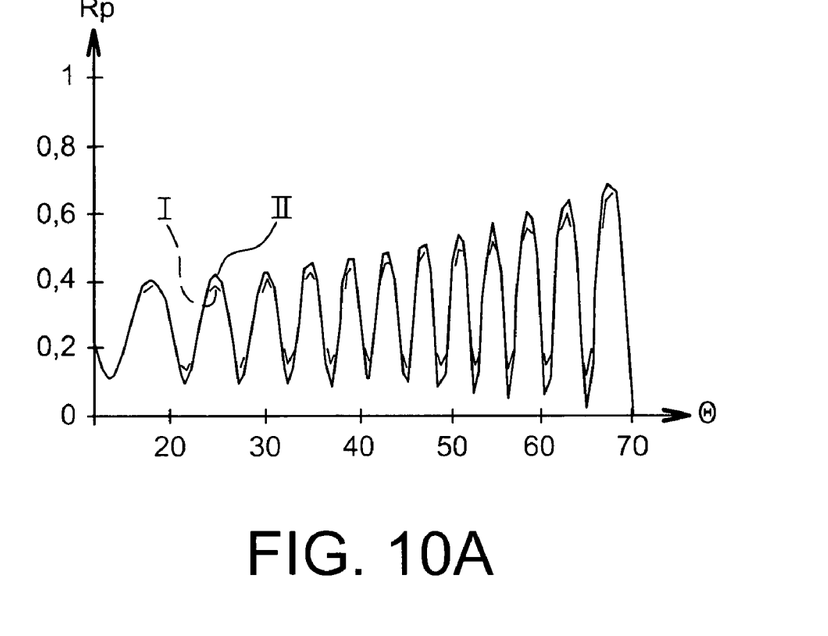
Figure 10B:
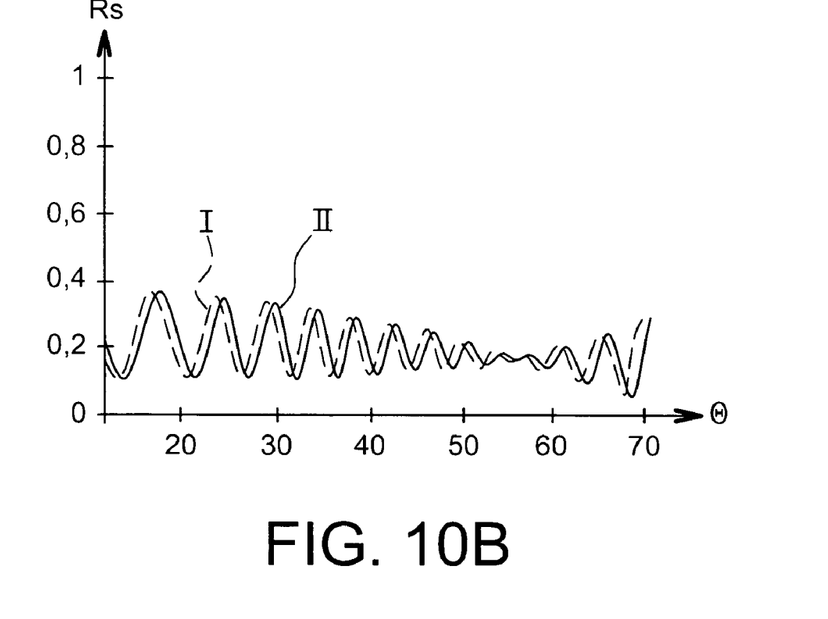

This example is shown in FIGS. 10A and 10B and relates to the characterisation of a single layer of silica (10 μm), the substrate being silicon.

In FIGS. 10A and 10B, the curves $R_P$ and $R_S$ are given as a function of $\theta$. The measurement curve is the curve II and the theoretical curve the curve I.

This example, and the one that follows, show that the invention allows identification of the thickness of a single layer of great thickness (more than 2 μm or 3 μm). Such a characterisation is very difficult to achieve via ellipsometry.

$h(2)=9869.3;$ $GOF(x^2)=0.99936$

EXAMPLE 2-6

Figure 11A:
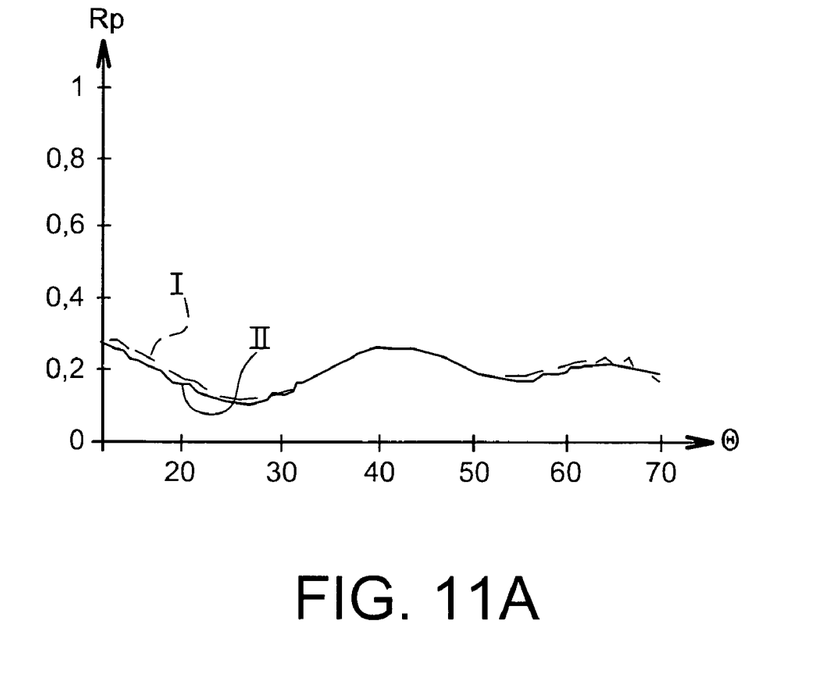
Figure 11B:
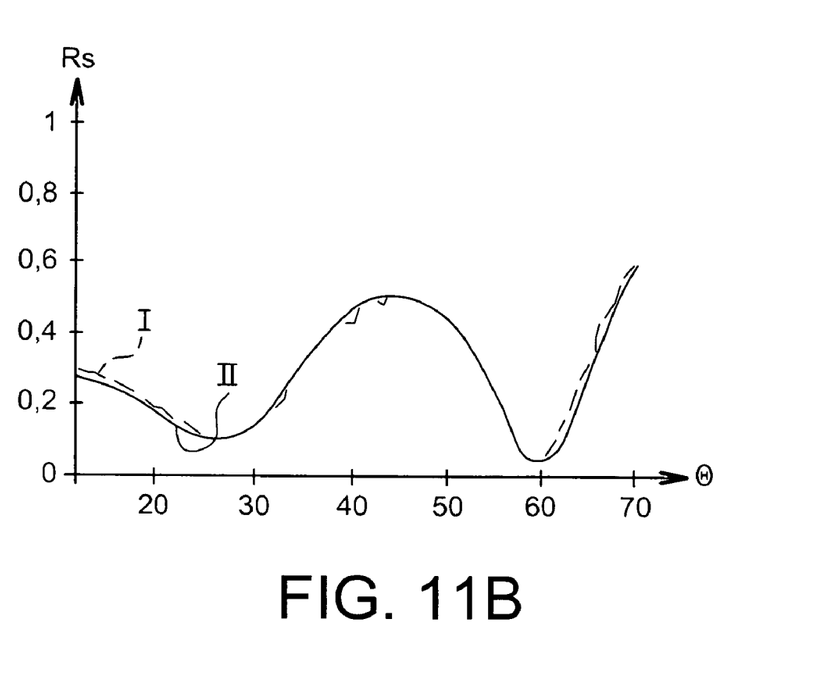

This example is shown in FIGS. 11A and 11B and also relates to a single layer structure, in particular a single layer of silica (1248 nm), on a silicon substrate.

$h(2)=1242.6;$ $GOF(x^2)=0.99991$

EXAMPLE 2-7

Figure 12A:
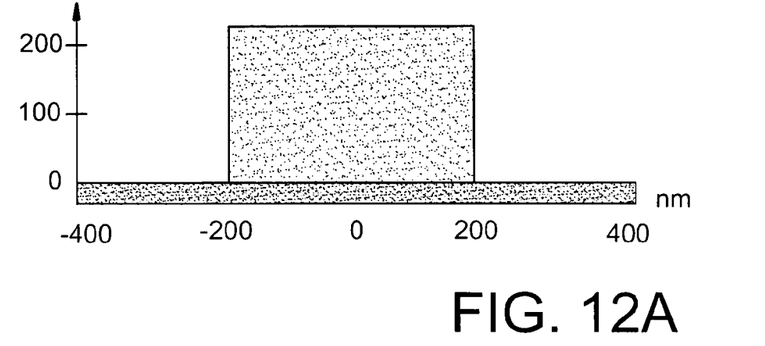
Figure 12B:
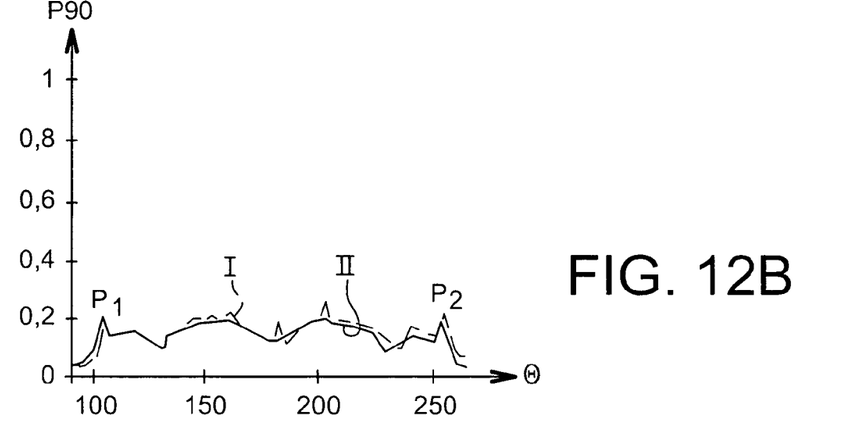
Figure 12C:
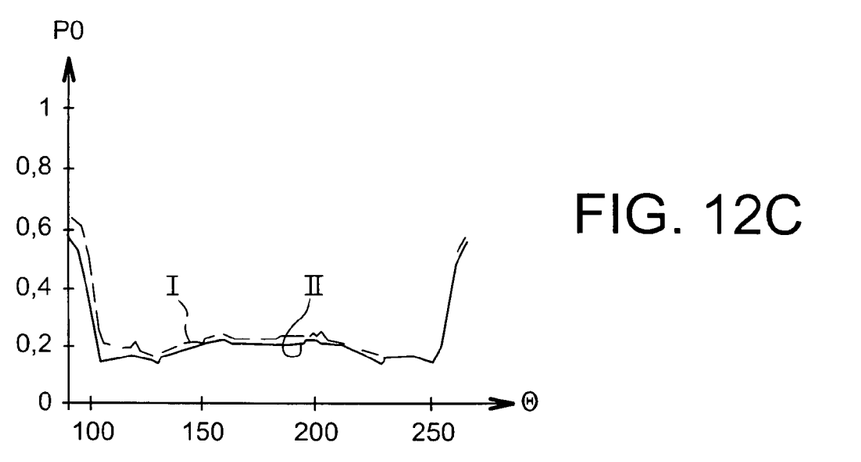

This example is shown in FIGS. 12A to 12C and relates to the characterisation of a resin grating of theoretical width 400 nm for a theoretical period of 800 nm. The measurement was taken on a sample of diameter 150 μm for $\theta=70°$, with two different polarisers (for $P_0$ and $P_{90}$). FIGS. 12B and 12C show $P_{90}$ and $P_0$ as a function of $\phi$.

Again we have the two peaks $P_1$, $P_2$ characteristic of the grating resonance.

$f(1)=358.7; h(1)=228.7$ $GOF(x^2)=0.99947$

EXAMPLE 2-8

Figure 13A:
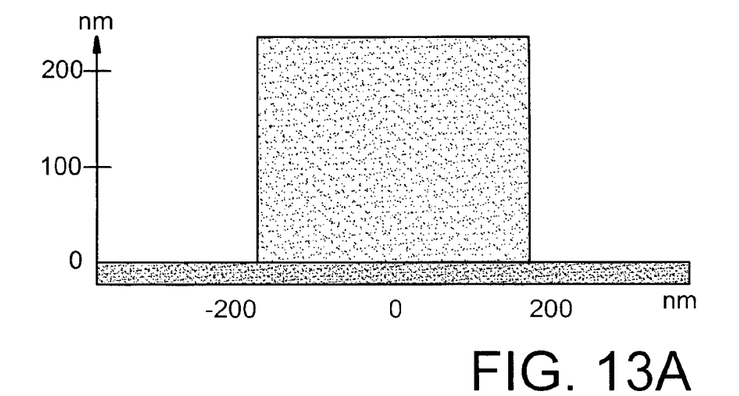
Figure 13B:
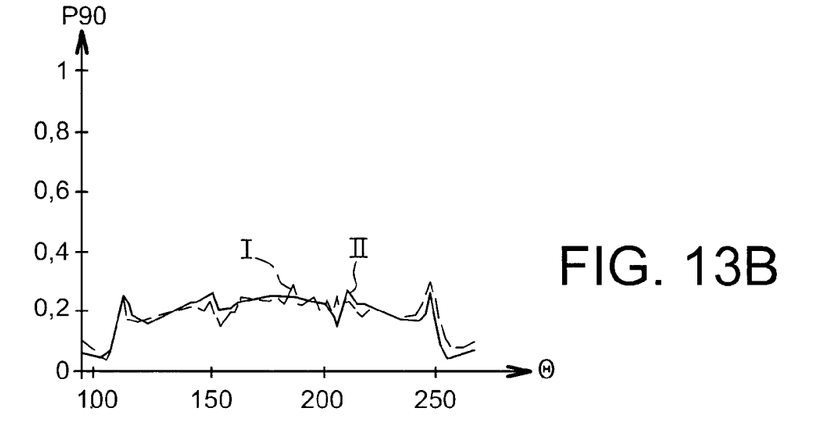
Figure 13C:
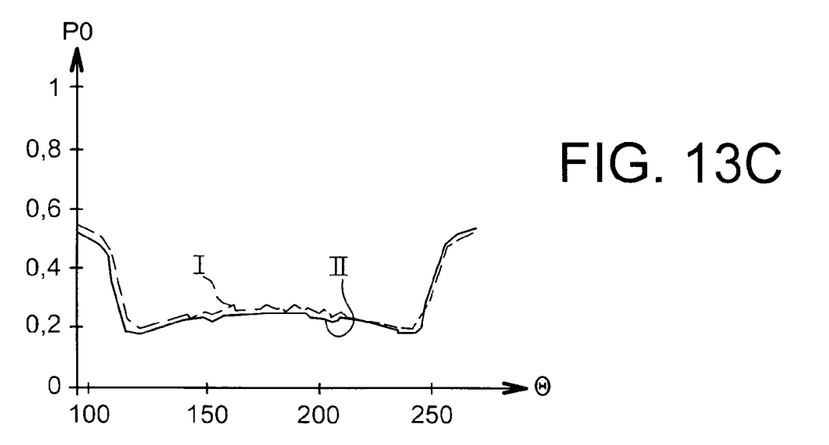

This example is shown in FIGS. 13A to 13C and relates to the characterisation of a resin grating of theoretical width 300 nm for a theoretical period of 600 nm. The measurement was taken on a sample of diameter 150 µm (for θ=70°). FIGS. 13B and 13C show $P_{90}$ and $P_0$ as a function of φ. Again we have the two peaks $P_1$, $P_2$ characteristic of the grating resonance.

$$f(1)=276.4; h(1)=229.9$$

$$GOF(x^2)=0.99966$$

The invention claimed is:

1. A device for measuring at least one characteristic of an object with a grating, the characteristic being a dimensional and/or structural characteristic, the device comprising:
 means for forming an optical Fourier transform image of an elemental surface of the object in a Fourier image focal plane;
 transfer means for transferring the optical Fourier transform image of the elemental surface to detection means;
 means for defining a geometry of the elemental surface; and
 processing means for determining at least a grating pitch of the object from information provided by the detection means.

2. A device according to claim 1, further comprising said detection means.

3. A device according to claim 1, wherein said means for defining the geometry of said elemental surface comprises a diaphragm.

4. A device according to claim 3, wherein said diaphragm has an aperture with a diameter of between 40 µm and 500 µm.

5. A device according to claim 1, further comprising a radiation source for illuminating the elemental surface of the object.

6. A device according to claim 5, wherein said radiation source has weak spatial coherence.

7. A device according to claim 5, wherein said radiation source has power of between 100 mW and 500 mW.

8. A device according to claim 5, wherein said radiation source has a small spectral width.

9. A device according to claim 8, wherein said radiation source has a spectral width of less than or equal to 10 nm.

10. A device according to claim 5, wherein the elemental surface of the object is illuminated from a Fourier plane.

11. A device according to claim 1, further comprising means for selectively illuminating the surface of the object.

12. A device according to claim 11, wherein said means for selectively illuminating includes a mask having a radial slot.

13. A device according to claim 11, wherein said means for selectively illuminating includes a mask having a slot in a circle arc.

14. A device according to claim 13, wherein said slot allows illumination along an angular arc of 180°.

15. A device according to claim 1, wherein said processing means employs an RCWA calculation.

16. A device according to claim 1, wherein said processing means calculates a theoretical intensity distribution for a given incident light and given grating pitch of the object, then compares the theoretical distribution with an intensity distribution and modifies the given grating pitch of the object if the result of the comparison is not satisfactory.

17. A device according to claim 1, wherein the geometry of the elemental surface is defined independently of a numerical aperture of the transfer means.

18. A device according to claim 1, wherein the processing means further determines at least one of a thickness of a single layer of said object, a dimension of said object, a surface roughness of said object, or a lateral roughness of said object.

19. A device according to claim 18, wherein the object is a nanostructure.

20. A process for measuring at least one dimensional and/or structural characteristic of an object with a grating that has an elemental surface illuminated by radiation, comprising:
 forming an optical Fourier transform image of the illuminated elemental surface in a Fourier image focal plane;
 transferring the image to detection means;
 processing data provided by the detection means so as to determine at least a grating pitch of the object.

21. A process according to claim 20, wherein the object is a one dimensional or two-dimensional grating, or a layer additionally including at least one single or biperiodic grating or a biomimetic membrane, or includes at least two superimposed gratings with a lateral offset.

22. A process according to claim 20, wherein the object includes a grating with a line width of between 10 nm and 10 µm.

23. A process according to claim 20, wherein the object includes a single layer with a thickness of between 10 nm and 100 µm.

24. A process according to claim 20, wherein the surface of the object is illuminated with a radiation having a power of between 100 mW and 500 mW.

25. A process according to claim 20, wherein the surface of the object is illuminated selectively.

26. A process according to claim 25, wherein the surface of the object is illuminated selectively and angularly.

27. A process according to claim 20, wherein the illuminated part of the surface of the object has a maximum dimension or a diameter, in the plane of the surface, of less than 500 µm.

28. A process according to claim 20, wherein the surface of the object is illuminated from a variable azimuthal direction.

29. A process according to claim 20, wherein the data provided by said detection means is processed by employing an RCWA calculation.

30. A process according to claim 20, wherein the data provided by said detection means is processed by calculating a theoretical intensity distribution for a given incident light and given grating pitch of the object, then comparing the theoretical distribution with an intensity distribution and modifying the given grating pitch of the object if the result of the comparison is not satisfactory.

31. A process according to claim 20, wherein the image formed on said detection means includes at least a 0 order component.

32. A process according to claim 31, wherein the image formed on said detection means additionally includes at least one component of another order.

33. A process according to claim 20, wherein an elemental surface of the object is illuminated from a Fourier plane.

34. A process according to claim 20, wherein a geometry of the elemental surface of the object is defined independently of a numerical aperture used to form the optical Fourier transform image.

35. A process according to claim 20, wherein the grating of the object includes has a line width of between 50 nm and 1 µm.

36. A process according to claim 20, wherein the object includes a single layer with a thickness of between 50 nm and 1 µm.

37. A device for measuring at least one characteristic of an object with a grating, the characteristic being a dimensional and/or structural characteristic, the device comprising:
- a measurement objective forming an optical Fourier transform image of an elemental surface of the object in a Fourier image focal plane;
- a transfer objective forming the optical Fourier transform image of the elemental surface on detection means;
- a diaphragm defining a geometry of the elemental surface;
- a processor determining at least a grating pitch of the object from information provided by said detector, said processor calculating a theoretical intensity distribution for a given incident light and given grating pitch of the object, then comparing the theoretical distribution with an intensity distribution and modifying the given grating pitch of the object if the result of the comparison is not satisfactory;
- a detector;
- a radiation source for illuminating an elemental surface of the object; and
- a mask to selectively illuminate the surface of the object.

38. A device according to claim 37, wherein the diaphragm has an aperture with a diameter of between 40 µm and 500 µm.

39. A device according to claim 37, wherein the radiation source has weak spatial coherence.

40. A device according to claim 37, wherein the radiation source has power of between 100 mW and 500 mW.

41. A device according to claim 37, wherein the radiation source is of small spectral width.

42. A device according to claim 41, wherein the radiation source has a spectral width of less than or equal to 10 nm.

43. A device according to claim 37, wherein an elemental surface of the object is illuminated from a Fourier plane.

44. A device according to claim 37, wherein the mask has a radial slot.

45. A device according to claim 37, wherein the mask has a slot in a circle arc.

46. A device according to claim 45, wherein the slot allows illumination along an angular arc of 180°.

47. A device according to claim 45, wherein said processor employs an RCWA calculation.

48. A device for measuring at least one characteristic of an object with a grating, the characteristic being a dimensional and/or structural characteristic, the device comprising:
- a measurement objective configured to form an optical Fourier transform image of an elemental surface of the object in a Fourier image focal plane;
- a transfer objective configured to transfer the optical Fourier transform image of the elemental surface to a detector;
- a diaphragm configured to define a geometry of the elemental surface; and
- a processor configured to determine a grating pitch of the object from information provided by the detector,
- wherein said processor is configured to calculate a theoretical intensity distribution for a given incident light and given grating pitch of the object, and to compare the theoretical distribution with an intensity distribution and modify the given grating pitch of the object if the result of the comparison is not satisfactory.

* * * * *